United States Patent
Rölle et al.

(10) Patent No.: US 9,754,084 B2
(45) Date of Patent: Sep. 5, 2017

(54) METHOD FOR SELECTING PHOTOINITIATOR SYSTEMS

(71) Applicant: Covestro Deutschland AG, Leverkusen (DE)

(72) Inventors: Thomas Rölle, Leverkusen (DE); Horst Berneth, Leverkusen (DE); Friedrich-Karl Bruder, Krefeld (DE); Thomas Fäcke, Leverkusen (DE); Marc-Stephan Weiser, Leverkusen (DE); Dennis Hönel, Zülpich-Wichterich (DE); Christian Diedrich, Düsseldorf (DE)

(73) Assignee: Covestro Deutschland AG, Leverkusen (DE)

(*) Notice: Subject to any disclaimer, the term of this patent is extended or adjusted under 35 U.S.C. 154(b) by 157 days.

(21) Appl. No.: 14/432,333

(22) PCT Filed: Sep. 27, 2013

(86) PCT No.: PCT/EP2013/070163
§ 371 (c)(1),
(2) Date: Mar. 30, 2015

(87) PCT Pub. No.: WO2014/053408
PCT Pub. Date: Apr. 10, 2014

(65) Prior Publication Data
US 2015/0261938 A1    Sep. 17, 2015

(30) Foreign Application Priority Data
Oct. 2, 2012   (EP) ..................... 12187040

(51) Int. Cl.
*G01N 33/48* (2006.01)
*G01N 33/50* (2006.01)
(Continued)

(52) U.S. Cl.
CPC ............. *G06F 19/704* (2013.01); *G03H 1/02* (2013.01); *G06F 19/701* (2013.01); *G03H 2260/12* (2013.01); *G06F 19/702* (2013.01)

(58) Field of Classification Search
None
See application file for complete search history.

(56) References Cited

U.S. PATENT DOCUMENTS

| 3,573,289 A | 3/1971 | Straley et al. |
| 4,419,511 A | 12/1983 | Raue |

(Continued)

FOREIGN PATENT DOCUMENTS

| EP | 58 863 A1 | 9/1982 |
| EP | 0 671 393 A1 | 9/1995 |

(Continued)

OTHER PUBLICATIONS

Fouassier, et al., "Photopolymerization Reactions Under Visible Lights: Principle, Mechanisms and Examples of Applications", *Progress in Organic Coatings*, vol. 47, pp. 16-36 (2003).

(Continued)

*Primary Examiner* — Russell S Negin
(74) *Attorney, Agent, or Firm* — Drinker Biddle & Reath LLP

(57) ABSTRACT

The invention relates to a method of selecting photoinitiator systems comprising at least one sensitizer and at least one coinitiator, for photopolymer formulations for producing holographic media.

8 Claims, 3 Drawing Sheets shows the measurement set-up to test the holographic properties for wavelengths of 633 and 532 nm.

(51) Int. Cl.
*G06F 19/00* (2011.01)
*G03H 1/02* (2006.01)

(56) References Cited

U.S. PATENT DOCUMENTS

2008/0145790 A1  6/2008  Baumann et al.
2012/0237856 A1  9/2012  Rölle et al.

FOREIGN PATENT DOCUMENTS

EP    1 253 148 A2     10/2002
WO    WO-9514689 A1     6/1995
WO    WO-2008125229 A1 10/2008

OTHER PUBLICATIONS

Aydin et al., "Mechanistic Study of Photoinitiated Free Radical Polymerization Using Thioxanthone Thioacetic Acid as One-Component Type II Photoinitiator", *Macromolecules*, vol. 38, pp. 4133-4138 (2005).
International Search Report for PCT/EP2013/070163 mailed Jan. 7, 2014.

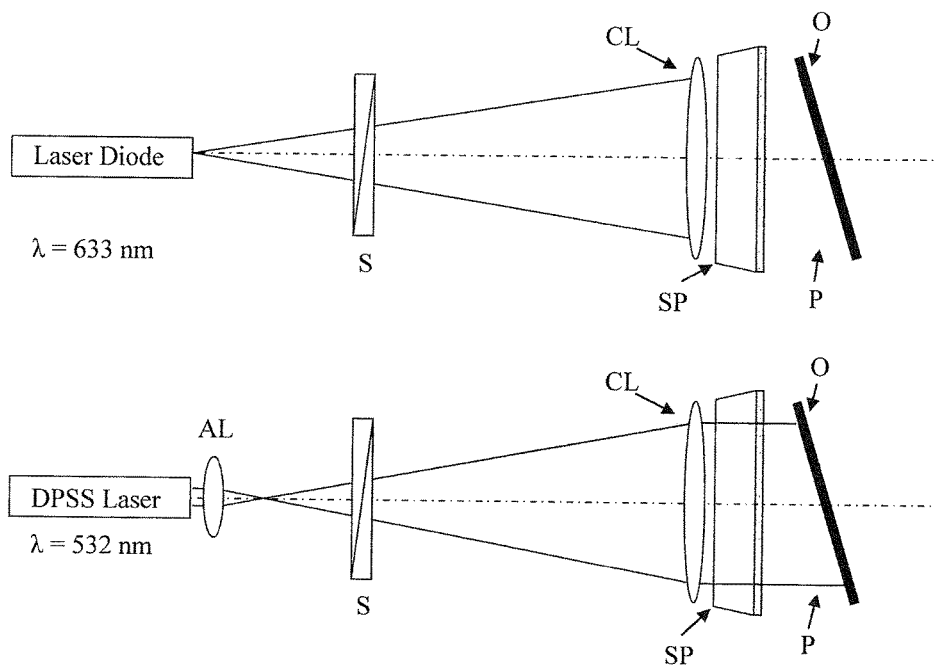
Figure 1 shows the measurement set-up to test the holographic properties for wavelengths of 633 and 532 nm.

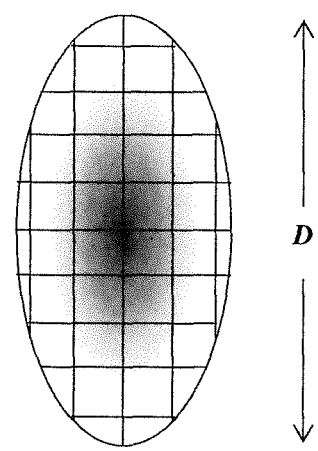
Figure 2 shows the elliptical shape of a hologram written under Figure 1.

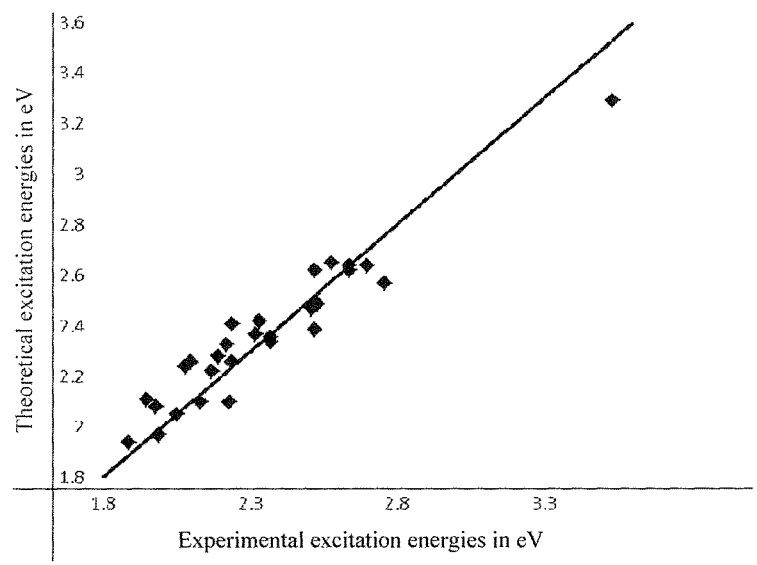
Figure 3 shows a plot of the theoretical versus the experimental excitation energies of contemplated example dyes F1 – F28.

METHOD FOR SELECTING PHOTOINITIATOR SYSTEMS

CROSS-REFERENCE TO RELATED APPLICATIONS

This application is a national stage application (under 35 U.S.C. §371) of PCT/EP2013/070163, filed Sep. 27, 2013, which claims benefit of European Application No. 12187040.6, filed Oct. 2, 2012, both of which are incorporated herein by reference in their entirety.

The invention relates to a method of selecting photoinitiator systems comprising at least one sensitizer and at least one coinitiator, for photopolymer formulations for producing holographic media.

Photopolymer formulations of the type mentioned at the beginning are known in the prior art. WO 2008/125229 A1, for instance, describes a photopolymer formulation comprising a polyol component, a polyisocyanate component, a writing monomer based on acrylate and also photoinitiators containing a coinitiator and a dye. In the cured state, the writing monomer and the photoinitiators form a spatially isotropic distribution embedded in the polyurethane matrix formed from polyol and polyisocyanate components.

The uses of photopolymer formulations are decisively determined by the refractive index modulation $\Delta n$ produced in the photopolymer by holographic exposure. In holographic exposure, the interference field of signal light beam and reference light beam (in the simplest case, that of two plane waves) is mapped into a refractive index grating by the local photopolymerization of, for example, high refractive index acrylates at loci of high intensity in the interference field. The refractive index grating in the photopolymer (the hologram) contains all the information of the signal light beam. Illuminating the hologram with only the reference light beam will then reconstruct the signal. The strength of the signal thus reconstructed relative to the strength of the incident reference light is diffraction efficiency, DE in what follows.

In the simplest case of a hologram resulting from the superposition of two plane waves, the DE is the ratio of the intensity of the light diffracted on reconstruction to the sum total of the intensities of the incident reference light and the diffracted light. The higher the DE, the greater the efficiency of a hologram with regard to the amount of reference light needed to visualize the signal with a fixed brightness.

When the hologram is illuminated with white light, for example, the width of the spectral range which can contribute to reconstructing the hologram is likewise only dependent on the layer thickness d. The relationship which holds is that the smaller the d, the greater the particular acceptance widths. Therefore, to produce bright and easily visible holograms, it is generally desirable to seek a high $\Delta n$ and a low thickness d while maximizing DE. That is, increasing $\Delta n$ increases the latitude to engineer the layer thickness d without loss of DE for bright holograms. Therefore, the optimization of $\Delta n$ is of outstanding importance in the optimization of photopolymer formulations (P. Hariharan, Optical Holography, 2nd Edition, Cambridge University Press, 1996).

In order that a very high $\Delta n$ and DE may be realized for holograms, the matrix polymers and writing monomers of a photopolymer formulation should in principle be chosen such that there is a very large difference in their refractive indices. One possible method of realization is to use matrix polymers having a very low refractive index and writing monomers having a very high refractive index. Suitable matrix polymers of low refractive index are for example polyurethanes obtainable by reaction of a polyol component with a polyisocyanate component.

In addition to high DE and $\Delta n$ values, however, another important requirement for holographic media from photopolymer formulations is that the matrix polymers be highly crosslinked in the final medium. When the degree of crosslinking is too low, the medium will lack adequate stability. One consequence of this is to appreciably reduce the quality of holograms inscribed in the media. In the worst case, the holograms may subsequently even be destroyed.

It is further very important, in particular for the large scale industrial production of holographic media from photopolymer formulations, that the photoinitiator system used should be optimally adapted to the wavelength of commercially available laser light sources and should enable light to be converted into efficient chain-starter molecules at very high quantum efficiency.

Yet media obtained from the known photopolymer formulations are frequently observed to be insufficiently wavelength selective. In addition, long exposure times or high doses of light are needed in many cases to achieve even the minimum necessary DE and $\Delta n$ values. Quality issues may accordingly present with media obtained from the known photopolymer formulations, while longer exposure times during large scale industrial manufacture are associated with appreciable expense and inconvenience.

A multiplicity of quantum-chemical procedures have been described to estimate chemical-reaction energies. The choice of any one procedure for a given problem depends on the accuracy requirements and also the available computation time. Very accurate methods, for example the Coupled Cluster Singles Doubles with perturbation-theoretical Triples correction CCSD(T) (T. Helgaker, P. Jørgensen and J, Olsen; Molecular Electronic-Structure Theory; Wiley, New York, 2000), also have very high computation-time requirements. Since the computation-time requirement of such procedures, moreover, increases with the seventh power of the size of the system ($O(N^7)$), such procedures are generally unusable for comparatively large molecules having more than 10-15 heavy atoms. Density-functional theory (DFT) methods (R. G. Bak and W. Yang; Density-Functional Theory of Atoms and Molecules; Oxford University Press, Oxford 1989) are used instead, although their distinctly higher efficiency comes at a loss of accuracy.

Very many new DFT methods have been developed over the last two decades, all with inherent strengths and weaknesses. The exact technical form of a DFT computation must accordingly be adapted to the problem to be investigated. What must be noted in relation to the method of the present invention is that all computed processes take place in the liquid or amorphous phase and that ionic and free-radical species are involved.

Continuum models such as the COnductor like Screening MOdel (COSMO) (A. Klamt and G. Schüürmann; *J. Am. Chem. Soc. Perkin Trans II*; 1993, 799) have become established in quantum chemistry for the simple description of liquid phases. The environment of a molecule is described in terms of a polarizable continuum in these models. This method frequently provides good results particularly in solvents having a low density of hydrogen bonds.

Various applications of the described methods to calculate reaction energies have been published (W. Koch and M. C. Holthausen; A Chemist's Guide to Density Functional Theory. Wiley-VHC, Weinheim).

As far as the description of electronically excited states is concerned, the above remarks regarding the computation of reaction energies hold to a significantly greater degree: The use of high-accuracy methods is limited to small molecules and is accordingly out of the question for dye molecules in photoinitiator systems. Therefore, DFT methods are also used in this context in the form of time-dependent density-functional theory (TDDFT) (M. E. Casida; Time-Dependent Density Functional Response Theory for Molecules; in: Recent Advances in Density Functional Methods, Vol. 1 (D. P. Chong, Ed.); *World Scientific: Singapore;* 155-192 (1995)). Simple hybrid density functionals are used here because they permit a computationally very efficient use. It is known from the literature (L. Goerigk and S. Grimme; *J. Chem. Phys.;* 132, 184103, (2010)) that these methods have large systematic errors for electronically excited states, these errors varying with the nature of the excited states (e.g. $\pi\pi^*$, Rydberg or d-d transitions in transition metals). Within any one class of excitation for a given application, the errors in the excitation energies can frequently be resolved by means of a global correction term. Since the excitations responsible for the coloredness of dyes are virtually all of the $\pi\pi^*$ type, the preconditions for a systematic correction are in place.

To estimate the suitability of a given dye/coinitiator pair for use as a photoinitiator system, the Rehm-Weller equation, formula (I), (D. Rehm, A. Weller, *Ber. Bunsenges. Physik. Chem.;* 73, 834, (1969)) has become established in the literature, a simplified version of which reads as follows:

$$\Delta G_{et} = E_{ox} - E_{red} - E_{0,0} + C, \qquad (I)$$

where
  $\Delta G_{et}$ is the free energy of electron transfer,
  $E_{ox}$ is the oxidation potential of the donor,
  $E_{red}$ is the reduction potential of the acceptor,
  $E_{0,0}$ is the excitation energy of the dye from the electronic ground state into the excited state relevant for the redox reaction, and
  C is the change in the electrostatic energy induced by the electron transfer process.

The electrochemical reduction and oxidation potentials are typically assumed in the literature for $E_{ox}$ and $E_{red}$ respectively. $E_{0,0}$ is approximated by the dye's excitation energy resulting from $\lambda_{max}$. C is assumed to be negligibly small in polar solvents.

According to the above, the direct application of the Rehm-Weller equation to the rational design of photoinitiator systems accordingly requires the experimental determination of $E_{ox}$, $E_{red}$ and $E_{0,0}$. When $\Delta G_{et}$ is negative, the system is potentially useful as photoinitiator. The method is unsuitable for substances which are not commercially available or are difficult to obtain chemically, since there is no simple way to estimate the required variables with sufficient accuracy without experiment. It must further be noted that using the experimental (singlet) excitation energy as $E_{0,0}$ creates a significant error, since the initiation reaction frequently takes place between the lowest triplet state of the dye and the coinitiator. The excitation energy measured in the UV/Vis, however, corresponds to a singlet→singlet excitation which, in the overwhelming majority of cases, is distinctly greater than the actually needed singlet→triplet excitation energy.

The problem addressed by the present invention was therefore that of developing a method of selecting photoinitiator systems comprising at least one sensitizer and at least one coinitiator, for photopolymer formulations for producing holographic media, which on the basis of the chemical structures which form a given photoinitiator system makes it possible to predict the performance thereof in a photochemical polymerization. Quantum-chemical computations should be used therein to correctly prescribe the electronic states of the compounds involved, including the above-described triplet state of the dye. The problem is solved by a method comprising a) selecting a photoinitiator system comprising at least one sensitizer and at least one coinitiator, b) establishing the photoinitiator system's reaction mechanism to include the transition of the sensitizer or sensitizers into an electronically excited state or, respectively, electronically excited states by absorption of electromagnetic radiation and the reaction which is referred to as the initiation reaction in subsequent steps whereby the sensitizer in the electronically excited state or the sensitizers in electronically excited states react(s) with the coinitiator(s) to form at least one free radical and further products, these products being dependent on the particular photoinitiator system, c) generating the three-dimensional molecular geometries of the sensitizer(s), of the coinitiator(s) and also of all initiation reaction intermediate and end products defined by the reaction mechanism and then subjecting these to a conformer analysis on the basis of a force field method, d) optimizing the molecular geometries of the structures from step c) having the lowest relative force field energy in each case quantum-chemically in the electronic ground state and determining the absolute electronic energies of the optimized structures, e) computing the excitation energies and oscillator strengths of the electronic absorption spectrum of the sensitizer(s) using the quantum-chemical time-dependent density-functional theory method and correcting the excitation energies for their systematic error, f) optimizing the molecular geometries of all sensitizers in the excited electronic states relevant with regard to the coinitiation reaction, on a density-functional theoretical level and determining the absolute electronic energies, g) computing the reaction energies of all component reactions of the mechanism established in step b), and h) classifying the photoinitiator system as suitable when the excitation frequency determined in step e) is in a ±50 nm interval around the exposure light wavelength and has an oscillator strength greater than 0.2 and when at the same time all reactive energies computed under g) are negative.

Step a) comprises selecting a photoinitiator system comprising at least one dye and at least one coinitiator. Step b) then comprises determining the reaction mechanism whereby the components of the photoinitiator system react with each other. In general, the reaction mechanism involves the absorption of electromagnetic radiation by at least one component (sensitizer) of the photoinitiator system to convert said component into an electronically excited state and the subsequent redox reaction of this excited compound with at least one further component (coinitiator) to release a reactive free radical. The reaction of this free radical with a monomer of the photopolymer formulation then concludes the initiation reaction.

In the simplest case of a multicomponent photoinitiator system, the photoinitiator system consists of one dye and one coinitiator. The reaction mechanism then presents as follows:

1) sensitizer+hv→sensitizer*
2) sensitizer*+coinitiator→sensitizer free-radical+coinitiator free-radical
3) coinitiator free-radical→coinitiator fragment+free radical 4) sensitizer free-radical+coinitiator→sensitizer fragment+coinitiator fragment The "sensitizer*" indicates an electronically excited state on the part of the sensitizer. Particularly the first excited singlet state ($S_1$) and the first triplet state ($T_1$) are relevant in the initiation reaction. An analogous approach is adopted for photoinitiator systems having more than two components. The redox properties of the compounds involved determine the specific reaction sequence. When, for example, the system contains a sensitizer which is easily reduced in the excited state and two or more coinitiators, the reaction with an oxidizable coinitiator must be assumed to be the primary initiation step, which is then followed by a secondary reaction with a reducible coinitiator to oxidize the sensitizer and thereby convert it back into its original form.

The reaction mechanism thus established is the basis for step c) and generating the three-dimensional molecular structures of all reactants, products and intermediates relevant in the component reactions and subjecting these to a conformer analysis. This involves, for example, a stochastic process wherein, in multiple successive steps, all rotatable bonds of a molecule are rotated by random angles and the resulting structures are subjected to a force field optimization. All conformers above a previously stipulated force field energy threshold value are discarded.

The remaining conformers are then subjected in step d) to a quantum-chemical geometric optimization on a density-functional theoretical (DFT) level. This is preferably done using the Becke-Perdew exchange correlation functional (BP86) (A. D. Becke; Phys. Rev. A; 38, 3098, (1998); J. Perdew; Phys. Rev. B; 33, 8822, (1986); S. H. Vosko, L. Wilk, M. Nusair; Can. J. Phys.; 58, 1200, (1980)) and also the Ahlrichs triple ζ valence basis set TZVP (A. Schäfer, C. Huber and R. Ahlrichs; J. Chem. Phys.; 100, 5829, (1994)), more preferably in addition the *COnductor like Screening MOdel* (COSMO) (A. Klamt and G. Schüümann; J. Am. Chem. Soc. Perkin Trans II; 1993, 799). The optimized geometries are then optionally subjected to a single point computation on a higher quantum-chemical level, preferably the DFT procedure using the BH-LYP functional (A. D. Becke; J. Chem. Phys.; 98, 1372, (1993)) and the Ahlrichs triple ζ valence basis set TZVP, more preferably with the COSMO model in addition.

The optimized geometries of the sensitizer conformers are the basis for subsequently performing time-dependent DFT computations to compute the electronic excitation energies ($\epsilon_i$) and oscillator strengths ($f_i$) of the excitations in the relevant region of the electromagnetic spectrum (step e)). Where two or more conformers were concerned, $\epsilon_i$ and $f_i$ are averaged in accordance with the Boltzmann weights resulting from the energies computed in step d).

The energies, likewise averaged across all contemplated conformers, of the sensitizer in the relevant electronic state for the primary coinitiation reaction are further determined on the same quantum-chemical level as used for the single point computations in step d) (step f)). The geometries of the sensitizers have to be optimized in the particular electronic states for this purpose. This, in the case of the lowest triplet state, can be done in a customary DFT geometric optimization. The case of a higher-excited triplet state or of the first excited singlet state requires a time-dependent DFT computation. The geometric optimization and also any subsequent single point computation are each performed on the same quantum-chemical level as also chosen under step d).

The energies thus computed can be used as the basis for step g) computing the reaction energies of all component reactions of the mechanism established in step b).

Step h), the concluding step, is used to verify whether:
1. The excitation energies determined in step e) lie within the spectral range desired for the planned use and the excitation has an oscillator strength greater than 0.2.
2. The reaction energies determined in step g) are negative.

If this is the case, then the photoinitiator system is classified as suitable by the method of the present invention.

In a first preferred embodiment of the method according to the present invention, the quantum-chemical geometric optimizations in steps d) and f) are effected using the DFT(BP86/TZVP) method and then DFT(BH-LYP/TZVP) single point computations are carried out.

In a similarly preferred embodiment, the quantum-chemical computations are carried out using the COnductor like Screening MOdels (COSMO).

In step e), it is more particularly the time-dependent DFT(BH-LYP/TZVP) procedure which can be used to compute the absorption spectra.

In a further development of the invention, the time-dependent DFT computations are carried out using the COSMO model.

In another preferred embodiment of the method according to the present invention, steps d) and f) consider all molecular geometries in a force field energy window of 0-8 kJ/mol instead of just the molecular geometry having the lowest force field energy and Boltzmann-weighted mean excitation energies, absorption strengths and overall energies are used not only to compute the absorption spectrum of the sensitizer in step e) but also to determine the reaction energies in step g), the Boltzmann weights being computed on a density-functional theoretical level, more preferably on the basis of DFT(BP86/TZVP) geometric optimizations with subsequent DFT(BH-LYP/TZVP) single point computations each using COSMO.

In a further preferred embodiment of the method according to the present invention, step e) utilizes the time-dependent DFT(BH-LYP/TZVP) procedure to compute the absorption spectra and the systematic error is assumed to be +0.7 electronvolt.

In a similarly preferred embodiment, step e) utilizes the time-dependent DFT(BH-LYP/TZVP) procedure in conjunction with the COSMO model and the systematic error is assumed to be +0.56 electronvolt.

The photopolymer formulation may preferably contain matrix polymers, more preferably crosslinked matrix polymers and even more preferably three-dimensionally crosslinked matrix polymers. It is very particularly preferable for the three-dimensionally crosslinked matrix polymers to be polyurethanes. These polyurethanes are obtainable by reacting at least one polyisocyanate component a) and at least one isocyanate-reactive component b).

The polyisocyanate component a) preferably comprises at least one organic compound which preferably has at least two NCO groups (polyisocyanate).

As polyisocyanate there can be used any compounds known per se to a person skilled in the art, or mixtures thereof. These compounds can be aromatic, araliphatic, aliphatic or cycloaliphatic based. The poluisocyanate component a) can also comprise monoisocyanates, i.e. organic compounds having an NCO group, and/or unsaturation-containing polyisocyanates, in minor amounts.

Suitable examples of polyisocyanates are butylene diisocyanate, hexamethylene diisocyanate (HDI), 2,2,4-trimethylhexamethylene diisocyanate and the isomers thereof (TMDI), isophorone diisocyanate (IPDI), 1,8-diisocyanato-4-(isocyanatomethyl)octane, the isomeric bis(4,4'-isocyanatocyclohexyl)methane and mixtures thereof having any desired isomer content, isocyanatomethyl-1,8-octane diisocyanate, 1,4-cyclohexylene diisocyanate, the isomeric cyclohexanedimethylene diisocyanates, 1,4-phenylene diisocyanate, 2,4- and/or 2,6-tolylene diisocyanate, 1,5-naphthylene diisocyanate, 2,4'- and/or 4,4'-diphenylmethane diisocyanate, triphenylmethane 4,4',4"-triisocyanate or any desired mixtures of the aforementioned compounds.

It is likewise possible to use monomeric di- or triisocyanates having urethane, urea, carbodiimide, acylurea, isocyanurate, allophanate, biuret, oxadiazinetrione, uretdione and/or iminooxadiazinedione structures.

Preference is given to polyisocyanates based on aliphatic and/or cycloaliphatic di- or triisocyanates.

It is particularly preferable for the polyisocyanates to comprise di- or oligomerized aliphatic and/or cycloaliphatic di- or triisocyanates.

Very particularly preferred polyisocyanates are isocyanurates, uretdiones and/or iminooxadiazinediones based on HDI, TMDI, 1,8-diisocyanato-4-(isocyanatomethyl)octane or mixtures thereof.

The polyisocyanate component a) may also comprise or consist of NCO-functional prepolymers. The prepolymers can have urethane, allophanate, biuret and/or amide groups. Prepolymers of this type are obtainable by reaction of polyisocyanates a1) with isocyanate-reactive compounds a2), for example.

Useful polyisocyanates a1) include all known aliphatic, cycloaliphatic, aromatic or araliphatic di- and triisocyanates. In addition, it is also possible to use the well-known higher molecular weight descendant products of monomeric di- and/or triisocyanates having a urethane, urea, carbodiimide, acylurea, isocyanurate, allophanate, biuret, oxadiazinetrione, uretdione or iminooxadiazinedione structure each individually or in any desired mixtures among each other.

Examples of suitable monomeric di- or triisocyanates useful as polyisocyanate a1) are butylene diisocyanate, hexamethylene diisocyanate, isophorone diisocyanate, trimethylhexamethylene diisocyanate (TMDI), 1,8-diisocyanato-4-(isocyanatomethyl)octane, isocyanatomethyl-1,8-octane diisocyanate (TIN), 2,4- and/or 2,6-toluene diisocyanate.

It may be preferable to use OH-functional compounds as isocyanate-reactive compounds a2). Polyols may be concerned in particular, The hereinbelow described polyols of component b) may most preferably be used as isocyanate-reactive compound a2).

It is likewise possible to use amines as isocyanate-reactive compounds a2). Examples of suitable amines are ethylenediamine, diethylenetriamine, triethylenetetramine, propylenediamine, diaminocyclohexane, diaminobenzene, diaminobisphenyl, difunctional polyamines, such as, for example, the Jeffamine® amine-terminated polymers in particular having number-average molar masses of up to 10 000 g/mol. Mixtures of the aforementioned amines can likewise be used.

It is also preferable for the isocyanate-reactive compounds a2) to have a number-average molar mass of $\geq 200$ and $\leq 10 000$ g/mol, more preferably $\geq 500$ and $\leq 8500$ g/mol and most preferably $\geq 1000$ and $\leq 8200$ g/mol.

The prepolymers of polyisocyanate component a) may more particularly have a residual content of free monomeric isocyanate <1% by weight, more preferably <0.5% by weight and most preferably <0.2% by weight.

Polyisocyanate component a) may also comprise mixtures of the aforementioned polyisocyanates and prepolymers.

It is optionally also possible for the polyisocyanate component a) proportionately to contain polyisocyanates, which are partially reacted with isocyanate-reactive ethylenically unsaturated compounds. $\alpha,\beta$-Unsaturated carboxylic acid derivatives, such as acrylates, methacrylates, maleates, fumarates, maleimides, acrylamides, and vinyl ethers, propenyl ethers, allyl ethers and compounds which contain dicyclopentadienyl units and have at least one group reactive towards isocyanates, are preferably used here as isocyanate-reactive ethylenically unsaturated compounds. Acrylates and methacrylates having at least one isocyanate-reactive group are particularly preferred.

The proportion of polyisocyanates which has been partially reacted with isocyanate-reactive ethylenically unsaturated compounds, in polyisocyanate component a), can be 0% to 99% by weight, preferably 0% to 50% by weight, more preferably 0% to 25% by weight and most preferably 0% to 15% by weight.

It may also be possible for polyisocyanate component a) to contain, completely or proportionately, polyisocyanates which are reacted completely or partially with blocking agents known from coating technology. The following may be mentioned as an example of blocking agents: alcohols, lactams, oximes, malonic esters, alkyl acetoacetates, triazoles, phenols, imidazoles, pyrazoles and amines, such as, for example, butanone oxime, diisopropylamine, 1,2,4-triazole, dimethyl-1,2,4-triazole, imidazole, diethyl malonate, ethyl acetoacetate, acetone oxime, 3,5-dimethylpyrazole, ε-caprolactam, N-tert-butylbenzylamine, cyclopentanone carboxyethyl ester or their mixtures.

It is particularly preferable for polyisocyanate component a) to comprise or consist of an aliphatic polyisocyanate or an aliphatic prepolymer and preferably an aliphatic polyisocyanate or aliphatic prepolymer having primary NCO groups.

Isocyanate-reactive component b) preferably comprises at least one organic compound having at least two isocyanate-reactive groups (isocyanate-reactive compound). In the context of the present invention, hydroxyl, amino or thiol groups are regarded as isocyanate-reactive groups.

Any system having on average at least 1.5 and preferably 2 to 3 isocyanate-reactive groups can be used as isocyanate-reactive component.

Isocyanate-reactive groups for the purposes of the present invention are preferably hydroxyl, amino or thiol groups, particular preference being given to hydroxyl compounds.

Examples of suitable polyfunctional isocyanate-reactive compounds are polyester polyols, polyether polyols, polycarbonate polyols, poly(meth)acrylate polyols and/or polyurethane polyols.

Suitable polyester polyols are, for example, linear polyester diols or branched polyester polyols, as are obtained in a known manner from aliphatic, cycloaliphatic or aromatic di- or polycarboxylic acids or their anhydrides with polyhydric alcohols having an OH functionality of $\geq 2$.

Examples of such di- or polycarboxylic acids or anhydrides are succinic, glutaric, adipic, pimelic, suberic, azelaic, sebacic, nonanedicarboxylic, decanedicarboxylic, terephthalic, isophthalic, o-phthalic, tetrahydrophthalic, hexahydrophthalic or trimellitic acid and acid anhydrides, such as o-phthalic, trimellitic or succinic anhydride or any desired mixtures thereof with one another.

Examples of suitable alcohols are ethanediol, di-, tri- or tetraethylene glycol, 1,2-propanediol, di-, tri- or tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, 1,8-octanediol, 1,10-decanediol, 1,12-dodecanediol, trimethylolpropane, glycerol or any desired mixtures thereof with one another.

The polyester polyols may also be based on natural raw materials, such as castor oil. It is also possible for the polyester polyols to be based on homo- or copolymers of lactones, as can preferably be obtained by an addition reaction of lactones or lactone mixtures, such as butyrolactone, ε-caprolactone and/or methyl-ε-caprolactone, with hydroxy-functional compounds, such as polyhydric alcohols having an OH functionality of ≥2 for example of the aforementioned type.

Such polyester polyols preferably have number-average molar masses of 400 to 4000 g/mol, particularly preferably of 500 to 2000 g/mol. Their OH functionality is preferably 1.5 to 3.5, particularly preferably 1.8 to 3.0.

Suitable polycarbonate polyols are obtainable in a manner known per se by reacting organic carbonates or phosgene with diols or diol mixtures.

Suitable organic carbonates are dimethyl, diethyl and diphenyl carbonate.

Suitable diols or mixtures comprise the polyhydric alcohols mentioned in connection with the polyester segments and having an OH functionality of ≥2, preferably 1,4-butanediol, 1,6-hexanediol and/or 3-methylpentanediol, or else polyesterpolyols can be converted into polycarbonate polyols.

Such polycarbonate polyols preferably have number-average molar masses of 400 to 4000 g/mol, particularly preferably of 500 to 2000 g/mol. The OH functionality of these polyols is preferably 1.8 to 3.2, particularly preferably 1.9 to 3.0.

Suitable polyether polyols are polyadducts of cyclic ethers with OH- or NH-functional starter molecules, said polyadducts optionally having a block structure.

Suitable cyclic ethers are, for example, styrene oxides, ethylene oxide, propylene oxide, tetrahydrofuran, butylene oxide, epichlorohydrin and any desired mixtures thereof.

Starters which may be used are the polyhydric alcohols mentioned in connection with the polyesterpolyols and having an OH functionality of ≥2 and primary or secondary amines and amino alcohols.

Preferred polyether polyols are those of the abovementioned type, exclusively based on propylene oxide or random or block copolymers based on propylene oxide with further 1-alkylene oxides, the proportion of 1-alkylene oxides being not higher than 80% by weight. Propylene oxide homopolymers and random or block copolymers which have oxyethylene, oxypropylene and/or oxybutylene units are particularly preferred, the proportion of the oxypropylene units, based on the total amount of all oxyethylene, oxypropylene and oxybutylene units, accounting for at least 20% by weight, preferably at least 45% by weight. Here, oxypropylene and oxybutylene comprise all respective linear and branched $C_3$- and $C_4$-isomers.

Such polyether polyols preferably have number-average molar masses of 250 to 10 000 g/mol, particularly preferably of 500 to 8500 g/mol and very particularly preferably of 600 to 4500 g/mol. The OH functionality is preferably 1.5 to 4.0, particularly preferably 1.8 to 3.1.

In addition, low molecular weight aliphatic, araliphatic or cycloaliphatic di-, tri- or polyfunctional alcohols having molecular weights below 500 g/mol, and being short-chain, i.e., containing 2 to 20 carbon atoms, are also useful as polyfunctional, isocyanate-reactive compounds as constituents of polyol component b).

These can be for example ethylene glycol, diethylene glycol, triethylene glycol, tetraethylene glycol, dipropylene glycol, tripropylene glycol, 1,2-propanediol, 1,3-propanediol, 1,4-butanediol, neopentyl glycol, 2-ethyl-2-butylpropanediol, trimethylpentanediol, positionally isomeric diethyloctanediols, 1,3-butylene glycol, cyclohexanediol, 1,4-cyclohexanedimethanol, 1,6-hexanediol, 1,2-cyclohexanediol, 1,4-cyclohexanediol, hydrogenated bisphenol A (2,2-bis(4-hydroxycyclohexyl)propane), 2,2-dimethyl-3-hydroxypropyl(2,2-dimethyl-3-hydroxypropionate). Examples of suitable triols are trimethylolethane, trimethylolpropane or glycerol. Suitable higher-functional alcohols are ditrimethylolpropane, pentaerythritol, dipentaerythritol or sorbitol.

It is particularly preferable for the polyol component to be a difunctional polyether, polyester or polyether-polyester block copolyester or a polyether-polyester block copolymer having primary OH functions. The photopolymer formulation may preferably also comprise a writing monomer.

The writing monomer may comprise at least one mono- and/or multifunctional writing monomer, in which case mono- and multifunctional acrylate writing monomers may be concerned in particular. It may be particularly preferable for the writing monomer to comprise at least one monofunctional urethane(meth)acrylate and one multifunctional urethane(meth)acrylate.

Acrylate writing monomers may be particularly compounds of general formula (II)

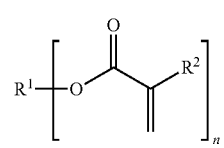

where in each case n is ≥1 and ≤4 and $R^1$ is a linear, branched, cyclic or heterocyclic unsubstituted or else optionally heteroatom-substituted organic radical and/or $R^2$ is hydrogen or a linear, branched, cyclic or heterocyclic unsubstituted or else optionally heteroatom-substituted organic radical. It is particularly preferable for $R^2$ to be hydrogen or methyl and/or $R^1$ to be a linear, branched, cyclic or heterocyclic unsubstituted or else optionally heteroatom-substituted organic radical.

It is similarly possible to add further unsaturated compounds such as α,β-unsaturated carboxylic acid derivatives such as acrylates, methacrylates, maleates, fumarates, maleim ides, acrylamides, also vinyl ether, propenyl ether, allyl ether and dicyclopentadienyl-containing compounds and also olefinically unsaturated compounds such as, for example, styrene, α-methylstyrene, vinyltoluene, olefins, for example 1-octene and/or 1-decene, vinyl esters, (meth)acrylonitrile, (meth)acrylamide, methacrylic acid, acrylic acid. Preference, however, is given to acrylates and methacrylates.

In general, esters of acrylic acid and methacrylic acid are designated as acrylates and methacrylates, respectively. Examples of acrylates and methacrylates which can be used are methyl acrylate, methyl methacrylate, ethyl acrylate, ethyl methacrylate, ethoxyethyl acrylate, ethoxyethyl methacrylate, n-butyl acrylate, n-butyl methacrylate, tert-butyl acrylate, tert-butyl methacrylate, hexyl acrylate, hexyl methacrylate, 2-ethylhexyl acrylate, 2-ethylhexyl methacrylate, butoxyethyl acrylate, butoxyethyl methacrylate, lauryl acrylate, lauryl methacrylate, isobornyl acrylate, isobornyl methacrylate, phenyl acrylate, phenyl methacrylate, p-chlorophenyl acrylate, p-chlorophenyl methacrylate, p-bromophenyl acrylate, p-bromophenyl methacrylate, 2,4,6-trichlorophenyl acrylate, 2,4,6-trichlorophenyl methacrylate, 2,4,6-tribromophenyl acrylate, 2,4,6-tribromophenyl methacrylate, pentachlorophenyl acrylate, pentachlorophenyl methacrylate, pentabromophenyl acrylate, pentabromophenyl methacrylate, pentabromobenzyl acrylate, pentabromobenzyl methacrylate, phenoxyethyl acrylate, phenoxyethyl methacrylate, phenoxyethoxyethyl acrylate, phenoxyethoxyethyl methacrylate, phenylthioethyl acrylate, phenylthioethyl methacrylate, 2-naphthyl acrylate, 2-naphthyl methacrylate, 1,4-bis(2-thionaphthyl)-2-butyl acrylate, 1,4-bis(2-thionaphthyl)-2-butyl methacrylate, propane-2,2-diylbis[(2,6-dibromo-4,1-phenylene)oxy(2-{[3,3,3-tris(4-chlorophenyl) propanoyl]oxy}propane-3,1-diyl)oxyethane-2,1-diyl] diacrylate, bisphenol A diacrylate, bisphenol A dimethacrylate, tetrabromobisphenol A diacrylate, tetrabromobisphenol A dimethacrylate and the ethoxylated analog compounds thereof, N-carbazolyl acrylates, to mention only a selection of acrylates and methacrylates which may be used.

It will be appreciated that urethane acrylates can also be used. Urethane acrylates are to be understood as meaning compounds having at least one acrylic acid ester group which additionally have at least one urethane bond. It is known that such compounds can be obtained by reacting a hydroxy-functional acrylic acid ester with an isocyanate-functional compound.

Examples of isocyanate-functional compounds which can be used for this purpose are aromatic, araliphatic, aliphatic and cycloaliphatic di-, tri- or polyisocyanates. It is also possible to use mixtures of such di-, tri- or polyisocyanates. Examples of suitable di-, tri- or polyisocyanates are butylene diisocyanate, hexamethylene diisocyanate (HDI), isophorone diisocyanate (IPDI), 1,8-diisocyanato-4-(isocyanatomethyl)octane, 2,2,4- and/or 2,4,4-trimethylhexamethylene diisocyanate, the isomeric bis(4,4'-isocyanatocyclohexyl)methanes and mixtures thereof having any desired isomer content, isocyanatomethyl-1,8-octane diisocyanate, 1,4-cyclohexylene diisocyanate, the isomeric cyclo-hexanedimethylene diisocyanates, 1,4-phenylene diisocyanate, 2,4- and/or 2,6-toluene diisocyanate, 1,5-naphthylene diisocyanate, 2,4'- or 4,4'-diphenylmethane diisocyanate, 1,5-naphthylene diisocyanate, m-methylthiophenyl isocyanate, triphenylmethane 4,4',4"-triisocyanate and tris(p-isocyanatophenyl)thiophosphate or derivatives thereof having a urethane, urea, carbodiimide, acylurea, isocyanurate, allophanate, biuret, oxadiazinetrione, uretdione or iminooxadiazinedione structure and mixtures thereof. Aromatic or araliphatic di-, tri- or polyisocyanates are preferred.

Suitable hydroxy-functional acrylates or methacrylates for the preparation of urethane acrylates are for example compounds such as 2-hydroxyethyl(meth)acrylate, polyethylene oxide mono(meth)acrylates, polypropylene oxide mono(meth)acrylates, polyalkylene oxide mono(meth)acrylates, poly(ε-capro-lactone) mono(meth)acrylates, such as, for example, Tone® M100 (Dow, Schwalbach, Germany), 2-hydroxypropyl(meth)acrylate, 4-hydroxybutyl(meth)acrylate, 3-hydroxy-2,2-dimethylpropyl(meth)acrylate, hydroxypropyl(meth)acrylate, 2-hydroxy-3-phenoxypropyl acrylate, the hydroxy-functional mono-, di- or tetraacrylates of polyhydric alcohols, such as trimethylolpropane, glycerol, pentaerythritol, dipentaerythritol, ethoxylated, propoxylated or alkoxylated trimethylolpropane, glycerol, pentaerythritol, dipentaerythritol or industrial mixtures thereof. 2-Hydroxyethyl acrylate, hydroxypropyl acrylate, 4-hydroxybutyl acrylate and poly(ε-caprolactone)mono(meth)acrylates are preferred. In addition, as isocyanate-reactive oligomeric or polymeric unsaturated compounds containing acrylate and/or methacrylate groups, alone or in combination with the abovementioned monomeric compounds, are suitable. The epoxy(meth)acrylates known per se containing hydroxyl groups and having OH contents of 20 to 300 mg KOH/g or polyurethane(meth)acrylates containing hydroxyl groups and having OH contents of 20 to 300 mg KOH/g or acrylated polyacrylates having OH contents of 20 to 300 mg KOH/g and mixtures thereof with one another and mixtures with unsaturated polyesters containing hydroxyl groups and mixtures with polyester(meth)acrylates or mixtures of unsaturated polyesters containing hydroxyl groups with polyester(meth)acrylates can likewise be used.

Preference is given particularly to urethane acrylates obtainable from the reaction of tris(p-isocyanatophenyl) thiophosphate and m-methylthiophenyl isocyanate with alcohol-functional acrylates such as hydroxyethyl(meth) acrylate, hydroxypropyl(meth)acrylate and hydroxybutyl (meth)acrylate.

In a further preferred embodiment, the photopolymer formulation additionally contains urethanes as plasticizers, which urethanes may be more particularly substituted with at least one fluorine atom.

The urethanes may preferably have general formula (III)

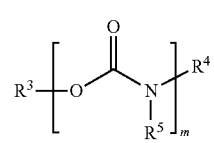

(III)

where m is ≥1 and ≤8 and $R^3$ is a linear, branched, cyclic or heterocyclic unsubstituted or else optionally heteroatom-substituted organic radical, and/or $R^4$ and $R^5$ are each independently hydrogen, while preferably at least one of $R^3$, $R^4$ and $R^5$ is substituted with at least one fluorine atom and more preferably $R^3$ is an organic radical having at least one fluorine atom. It is particularly preferable for $R^5$ to be a linear, branched, cyclic or heterocyclic organic radical which is unsubstituted or else optionally substituted with heteroatoms such as fluorine for example.

BRIEF DESCRIPTION OF DRAWINGS

FIG. 1 shows the measurement set-up to test the holographic properties for wavelengths of 633 and 532 nm.

FIG. 2 shows the elliptical shape of a hologram written under FIG. 1.

FIG. 3 shows a plot of the theoretical versus the experimental excitation energies of contemplated example dyes F1-F28.

EXAMPLES

The invention will now be more particularly described by means of the following examples. The synthesis and characterization of example molecules are described first, followed by their treatment in the method of the present invention.

Substances:

The dyes, salts, solvents and reagents used were obtained from chemical suppliers, unless their preparation is described hereinbelow.

| | |
|---|---|
| CGI-909 | tetrabutylammonium tris(3-chloro-4-methylphenyl)(hexyl)borate, [1147315-11-4] is a product made by BASF SE, Basle, Switzerland. |
| Desmorapid ® Z | dibutyltin dilaurate [77-58-7], product from Bayer MaterialScience AG, Leverkusen, Germany. |
| Desmodur ® N 3900 | product from Bayer MaterialScience AG, Leverkusen, DE, hexane diisocyanate-based polyisocyanate, proportion of iminooxadiazinedione at least 30%, NCO content: 23.5%. |
| Fomrez ® UL 28 | urethanization catalyst, commercial product of Momentive Performance Chemicals, Wilton, CT, USA. |
| Irgacure ® 250 | (4-methylphenyl)-[4-(2-methylpropyl)phenyl]iodonium hexafluorophosphate, [344562-80-7], 75% strength solution in propylene carbonate, is a product made by BASF SE, Basle, Switzerland |
| EDB | ethyl (4-dimethylamino)benzoate [10287-53-3], Sigma Aldrich |
| New Methylene Blue | C. I. Basic Blue 24, [as chloride: 1934-16-3], Sigma Aldrich |

Preparation of Components

Preparation of Polyol 1:

In a 1 L flask, 0.18 g of tin octoate, 374.8 g of ε-caprolactone and 374.8 g of a difunctional poly-tetrahydrofuran polyether polyol (equivalent weight 500 g/mol of OH) were initially charged and heated to 120° C. and maintained at this temperature until the solids content (the proportion attributed to the non-volatile constituents) was 99.5% by weight or higher. This was followed by cooling to obtain the product as a waxy solid.

Preparation of acrylate 1 (phosphorothioyltris(oxy-4,1-phenyleneiminocarbonyloxyethane-2,1-diyl) triacrylate)

In a 500 mL round-bottom flask, 0.1 g of 2,6-di-tert-butyl-4-methylphenol, 0.05 g of dibutyltin dilaurate (Desmorapid® Z, Bayer MaterialScience AG, Leverkusen, Germany) and 213.07 g of a 27% strength solution of tris(p-isocyanatophenyl)thiophosphate in ethyl acetate (Desmodur® RFE, product of Bayer MaterialScience AG, Leverkusen, Germany) were initially charged and heated to 60° C. Thereafter, 42.37 g of 2-hydroxyethyl acrylate were added dropwise and the mixture was further maintained at 60° C. until the isocyanate content had dropped below 0.1%. This was followed by cooling and complete removal of the ethyl acetate under reduced pressure to obtain the product as a partly crystalline solid.

Preparation of acrylate 2 (2-({[3-(methylsulphanyl)phenyl]carbamoyl}oxy)ethyl prop-2-enoate)

In a 100 mL round-bottom flask, 0.02 g of 2,6-di-tert-butyl-4-methylphenol, 0.01 g of Desmorapid® Z, and 11.7 g of 3-(methylthio)phenyl isocyanate were initially charged and heated to 60° C. Thereafter, 8.2 g of 2-hydroxyethyl acrylate were added dropwise and the mixture was further maintained at 60° C. until the isocyanate content had dropped below 0.1%. This was followed by cooling to obtain the product as a pale yellow liquid.

Preparation of additive 1 (bis(2,2,3,3,4,4,5,5,6,6,7,7-dodecafluoroheptyl)(2,2,4-trimethylhexane-1,6-diyl)biscarbamate)

In a round-bottom flask, 0.02 g of Desmorapid Z and 3.6 g of 2,4,4-trimethylhexane 1,6-diisocyanate were initially charged and heated to 70° C. This was followed by the dropwise addition of 11.39 g of 2,2,3,3,4,4,5,5,6,6,7,7-dodecafluoroheptan-1-ol and the mixture was further maintained at 70° C. until the isocyanate content had dropped below 0.1%. This was followed by cooling to obtain the product as a colourless oil.

Synthesis of dye F1: pyridine salt of 5-[5-(hexahydro-1,3-diethyl-4,6-dioxo-2-thioxo-5-pyrimidinyl)-2,4-propenylidene]-1,3-diethyl-2-thiobarbituric acid 4.00 g of 1,3-diethyl-2-thiobarbituric acid and 1.64 g of 1,1,3,3-tetramethoxypropane were stirred in 10 mL of pyridine at 90° C. for 10 h. Cooling was followed by dilution with 30 mL of toluene, filtration with suction, washing with 3×10 mL of toluene and finally 50 mL of water and vacuum drying at 50° C. to obtain 2.33 g (45.3% of theory) of a red crystallisate of the formula

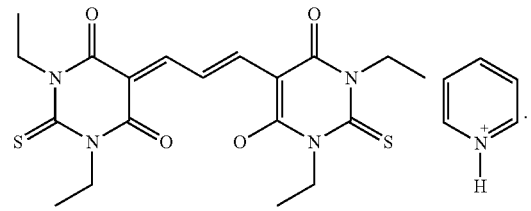

Production of Media to Determine the Holographic Properties

Example Medium 1

3.38 g of polyol component 1 were mixed with 2.00 g of acrylate 1, 2.00 g of acrylate 2, 1.50 g of additive 1, 0.10 g of CGI 909 (product from BASF SE, Basle, Switzerland), 0.010 g of New Methylene Blue (=F7) and 0.35 g of N-ethylpyrrolidone at 60° C. so that a clear solution was obtained. This was followed by cooling to 30° C., addition of 0.65 g of Desmodur® N3900 (commercial product of Bayer MaterialScience AG, Leverkusen, DE, hexane diisocyanate-based polyisocyanate, proportion of iminooxadiazinedione at least 30%, NCO content: 23.5%) and renewed mixing. Finally, 0.01 g of Fomrez UL 28 (urethanization catalyst, commercial product of Momentive Performance Chemicals, Wilton, Conn., USA) was added before renewed brief mixing. The liquid mass obtained was then poured onto a glass plate and covered there with a second glass plate. This sample specimen was left to lie at room temperature for 12 hours for curing.

Example Medium 2

3.38 g of polyol component 1 were mixed with 2.00 g of acrylate 1, 2.00 g of acrylate 2, 1.50 g of additive 1, 0.10 g of Irgacure® 250 (product from BASF SE, Basle, Switzerland), 0.10 g of EDB, 0.010 g of dye F1 and 0.35 g of N-ethylpyrrolidone at 60° C. so that a clear solution was obtained. This was followed by cooling to 30° C., addition of 0.65 g of Desmodur® N3900 (commercial product of Bayer MaterialScience AG, Leverkusen, DE, hexane diisocyanate-based polyisocyanate, proportion of iminooxadiazinedione at least 30%, NCO content: 23.5%) and renewed mixing. Finally, 0.01 g of Fomrez UL 28 (urethanization catalyst, commercial product of Momentive Performance Chemicals, Wilton, Conn., USA) was added before renewed brief mixing. The liquid mass obtained was then poured onto a glass plate and covered there with a second glass plate. This sample specimen was left to lie at room temperature for 12 hours for curing.

Holographic Exposure of Photopolymer Formulations:

A hologram was exposed into the photopolymer using a measurement set-up according to FIG. 1. The hologram in question was a monochromatic hologram at 633 nm or 532 nm laser wavelength. The example media obtained as described above were introduced into the measurement set-up by means of a sample holder.

The beam of a laser (emission wavelength 633 nm or 532 nm) was expanded to a diameter of ~3-4 cm by means of an optional expanding lens (AL) and the collimating lens (CL) placed downbeam of the shutter S. The diameter of the expanded laser beam was determined by the aperture of the opened shutter. Care was taken to ensure that the intensity distribution of the expanded laser beam was inhomogeneous. The edge intensity PR was accordingly~only half the intensity PZ at the centre of the expanded laser beam. P here was to be understood as meaning power/area. The expanded laser beam passed first through a glass plate placed as shearing plate (SP) at an oblique angle to the beam. The upwardly reflected interference pattern created by the two glass surface reflections of the SP was used to tell whether the laser emits stably in single mode. In that case, a pattern of dark and light stripes could be seen on a matte screen placed above the SP. Only if emission was single mode were holographic exposures performed. In the case of DPSS lasers, single mode was achievable by adjusting the pump current. The expanded beam passed through the photopolymer (P), which was at a slant of about 15°, this part forming the reference beam, before being reflected back into P by the object (O) arranged parallel to P. This part then formed the signal beam of the Denisyuk arrangement.

The interference of signal beam and reference beam in P created the hologram in the photopolymer. O consisted of a metal plate covered with white paper, with the paper side facing P. On the paper was a square grid created by black lines. The edge length of any one square was 0.5 cm. This grid was co-imaged in the hologram by the holographic exposure of P.

The average exposure dose $E_{ave}$ was set via the opening time t of S. With a fixed laser intensity I, therefore, t represented the variable proportional to $E_{ave}$. Since the expanded laser beam possessed an inhomogeneous (bell-shaped) distribution of intensity, there is variation in the local dose E to create the hologram in P. This, together with the slanted position of P and O relative to the optical axis, means that the written hologram possessed an elliptical shape. This is shown in FIG. 2.

Since O was a diffuse reflector, the hologram was easily reconstructed by illumination with a point light source (e.g. a torch or LED lamp). In this case, the photopolymer formulation contains an active photoinitiator. This finding is characterized in Table 2 as (J).

After the writing of the hologram, the photopolymer was bleached under UV radiation. For this, the samples taken from an aluminium bag in light-fast packaging were placed with the glass side up onto the conveyor belt of a UV unit and, while travelling at a belt speed of 2.5 m/min, were exposed twice under a Fusion UV 558434 KR 85 lamp at a nominal power density of 80 W/cm², with an energy density of ~2 J/cm² on the photopolymer.

Using the Method of the Present Invention to Test for Usefulness as Photoinitiator System Example 1

The operating assumption is that, for a given task, the photopolymer formulation is to be exposed with an HeNe laser having a wavelength of 630 nm. The method of the present invention will now be used to verify the suitability of the two-component initiator system New Methylene Blue (NMB F7)/CGI909 for the application described.

The reaction mechanism of the New Methylene Blue (NMB/F7)/CGI909 two-component initiator system consists of the following steps:
1. Light absorption by the dye. With transition from the electronic ground state ($S_0$) into the first excited singlet state ($S_1$).
2. Intersystem crossing into a triplet state of the dye and fast relaxation to the lowest triplet state ($T_1$).
3. Reaction of the dye molecule in the $T_1$ state with CGI909 to form a neutral NMB free-radical $NMB_{rad}$, a borane $BAr_3$ and also a hexyl free-radical $Hex_{rad}$ in accordance with the following reaction equation:

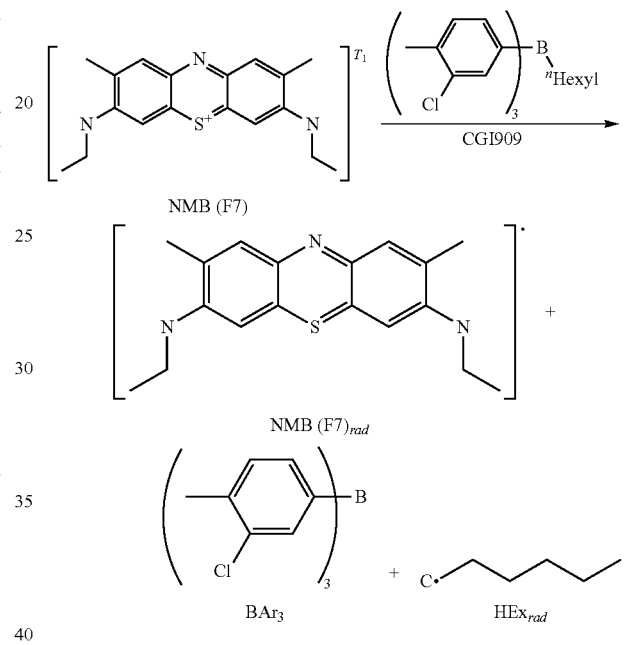

The three-dimensional structures of New Methylene Blue and CGI909 and also of the descendant products of CGI909 were subjected to a conformer analysis by means of the conformer module in the Materials Studio software package from Accelrys. The result of this analysis was that, in the present case, only the stablest conformer had to be considered in each case, since the molecules are very rigid apart from the hexyl free-radical. Therefore, the stablest conformer according to the force field computation performed in the conformer analysis was used in each case as starting point for the quantum-chemical computations.

The particular stablest conformers thus found were then geometrically optimized quantum-chemically in the electronic ground state in accordance with step d) of the method according to the present invention. This was done using the TURBOMOLE Version 6.1 software package. The computations were done on a density-functional theoretical level using the density functional BP86 and the base set TZVP. The COnductor like Screening MOdel (COSMO) continuum solvent model was also used. The molecular geometries thus obtained were then subjected to single point computations at the BH-LYP/TZVP+COSMO level. The result of this computation, i.e. absolute electronic energies at the DFT(BH-LYP/TZVP+COSMO//BP86/TZVP+COSMO) level (see Table 1), is used as described hereinbelow to compute the reaction energies of the initiation reaction.

TABLE 1

Table 1: Absolute electronic ground state energies of compounds involved in the NMB(F7)/CGI909 initiation reaction

| Compound | E(BH-LYP/TZVP + COSMO//BP86/ TZVP + COSMO)/Hartree |
|---|---|
| CGI909 | −2452.841810 |
| NMB(F7)$_{rad}$ | −1261.354348 |
| BPh$_3$ | −2216.337044 |
| Hex$_{rad}$ | −236.3315548 |

The next step (step e)) involved computing the electronic excitation energy of New Methylene Blue by means of time-dependent density functional theory and using the BH-LYP hybrid functional and the TZVP base set and also the COSMO model. The excitation energy turned out to be 2.53 eV and the oscillator strength (as per the long form of the dipole operator) as 1.08 units. The excitation energy is corrected for its systematic error of 0.56 eV, determined empirically on a large benchmark set of dyes, to 1.97 eV, which corresponds to a wavelength of 623 nm.

The last remaining energy to be computed is the absolute energy of the first triplet state of New Methylene Blue. This was likewise done on the DFT(BH-LYP/TZVP+COSMO//BP86/TZVP+COSMO) level and produced an energy of E($^3$NMB)=−1261.164863 Hartree.

The intersystem crossing of the dye from S$_0$ into the T$_1$ state is consistently negative. This means that it is only the reaction of New Methylene Blue in the triplet state with CGI909 to form the corresponding fragments which is decisive for the thermodynamic relevance of the two-component initiator system on the basis of the reaction mechanism described above. The thermodynamic relevance is apparent from the computed absolute energies as follows:

$$E_{coin} = E(NMB_{rad}) + E(Hex_{rad}) + E(BAr_3) - E(^3NMB) - E(CGI909)$$

$$= (-1261.354348 - 236.3315548 - 2216.337044 +$$

$$1261.164863 + 2452.841810)\text{Hartree}$$

$$= -0.016274 \text{ Hartree}$$

$$\approx -43 \text{ kJ/mol.}$$

Since the only relevant reaction energy in this example, $E_{coin}$, is negative, the computed absorption energy at 630 nm is in perfect agreement with the target value of 630 nm and the excitation at an oscillator strength of 1.08 units is above the threshold value of 0.2, the two-component initiator system NMB/CGI909 must be classified as suitable within the meaning of the method according to the present invention.

The initiator system proved to be holographically active in agreement with the prediction and the computed absorption wavelength of 630 nm is also in good agreement with the experimental value of 623 nm.

The preparation and testing of Example Medium I were repeated on media comprising the particular dyes indicated in Table 2, which likewise shows the results obtained with the method of the present invention.

TABLE 2

Theoretical and experimental absorption energies, theoretical absorption strengths (f$^1$) and coinitiation energies (see text) and experimental holographic activity of dyes in two-component initiator systems comprising CGI909.

| Dye example | Name | Absorption/eV Theory (E/f$^1$) | Exp. | Holographically active (yes/no) | E(CGI)/ (kJ/mol) | Structure |
|---|---|---|---|---|---|---|
| F2 | keto-coumarin | 2.64 f$^1$ = 1.90 | 2.70 | yes | −67 | 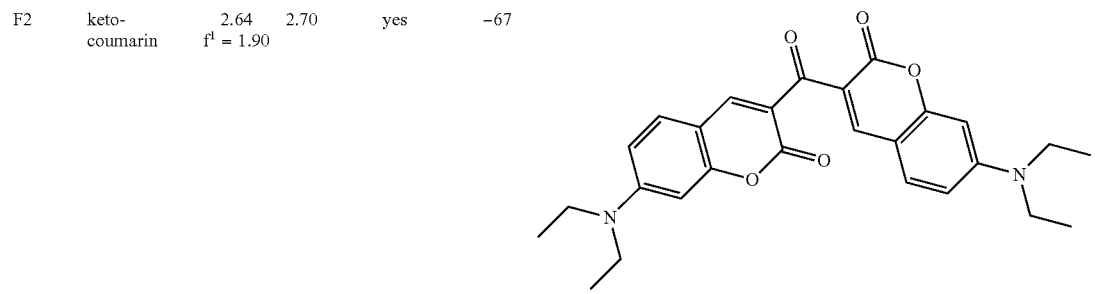 |
| F3 | Carbol Fuchsin | 2.41 f$^1$ = 0.79 | 2.24 | yes | −67 | 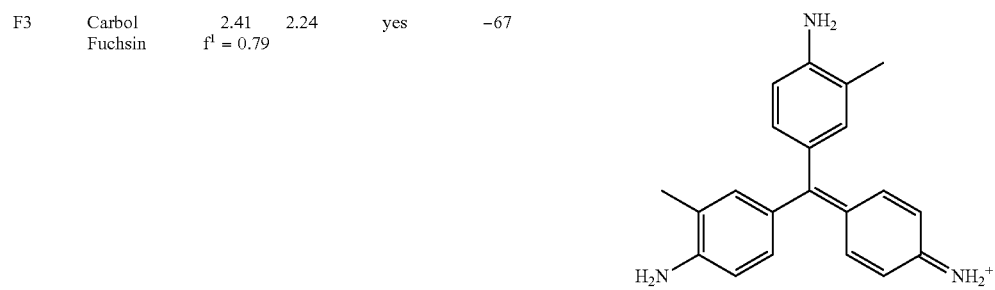 |

TABLE 2-continued

Theoretical and experimental absorption energies, theoretical absorption strengths (f¹) and coinitiation energies (see text) and experimental holographic activity of dyes in two-component initiator systems comprising CGI909.

| Dye example | Name | Absorption/eV Theory (E/f¹) | Exp. | Holographically active (yes/no) | E(CGI)/ (kJ/mol) | Structure |
|---|---|---|---|---|---|---|
| F4 | Rhodamine 6G | 2.36 $f^1 = 1.17$ | 2.37 | yes | −66 | 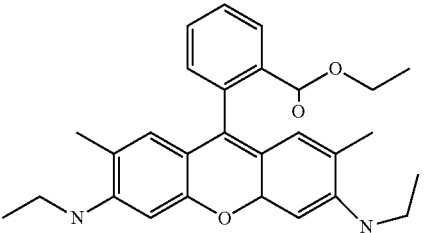 [SMILES: CCNC1=CC2Oc3cc(NCC)c(C)cc3C(c3ccccc3C(O)OCC)=C2C=C1C] |
| F5 |  | 2.22 $f^1 = 0.48$ | 2.17 | yes | −60 | 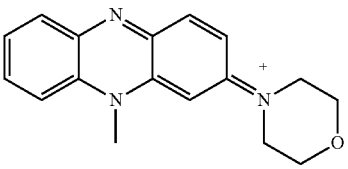 |
| F6 |  | 2.10 $f^1 = 1.05$ | 2.13 | yes | −59 | 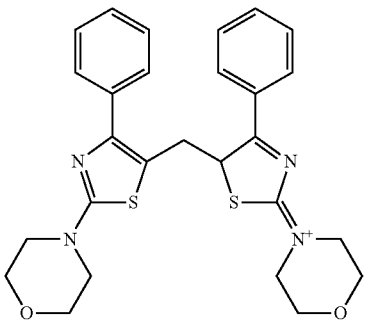 [SMILES: c1ccc(C2=NC(=[N+]3CCOCC3)SC2Cc2sc(N3CCOCC3)nc2-c2ccccc2)cc1] |
| F7 | New Methylene Blue | 1.97 $f^1 = 1.08$ | 1.99 | yes | −43 | 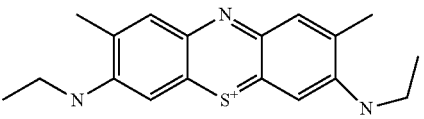 [SMILES: CCNc1cc2[s+]c3cc(NCC)c(C)cc3nc2cc1C] |
| F8 | crystal violet | 2.26 $f^1 = 0.98$ | 2.10 | yes | −42 | 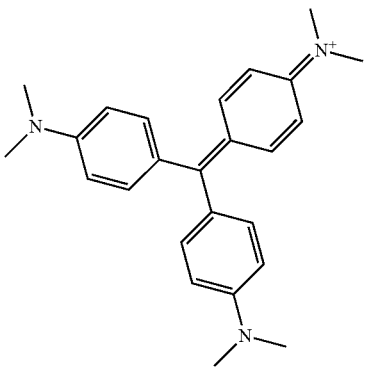 |
| F9 |  | 2.64 $f^1 = 1.00$ | 2.64 | yes | −41 | 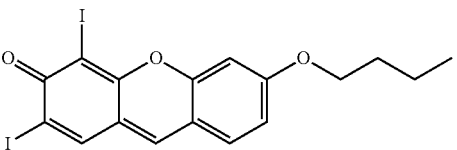 [SMILES: CCCCOc1ccc2cc3cc(I)c(=O)c(I)c-3oc2c1] |

TABLE 2-continued

Theoretical and experimental absorption energies, theoretical absorption strengths (f¹) and coinitiation energies (see text) and experimental holographic activity of dyes in two-component initiator systems comprising CGI909.

| Dye example | Name | Absorption/eV Theory (E/f¹) | Exp. | Holographically active (yes/no) | E(CGI)/ (kJ/mol) | Structure |
|---|---|---|---|---|---|---|
| F10 | Safranine O | 2.37<br>f¹ = 0.97 | 2.32 | yes | −40 | 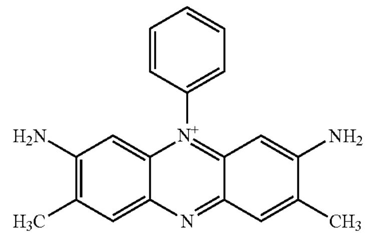 [SMILES: Cc1cc2nc3cc(C)c(N)cc3[n+](-c3ccccc3)c2cc1N] |
| F11 | | 2.10<br>f¹ = 1.22 | 2.23 | yes | −40 | 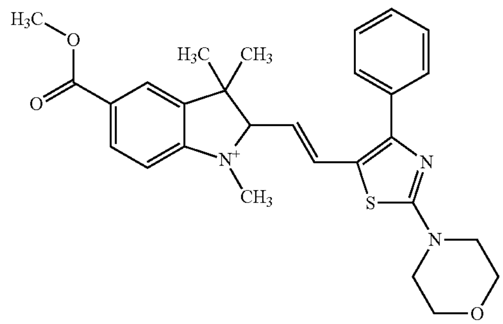 [SMILES: COC(=O)c1ccc2c(c1)C(C)(C)C(/C=C/c1sc(N3CCOCC3)nc1-c1ccccc1)[NH+]2C] |
| F12 | Brilliant Green | 2.08<br>f¹ = 1.20 | 1.98 | yes | −38 | 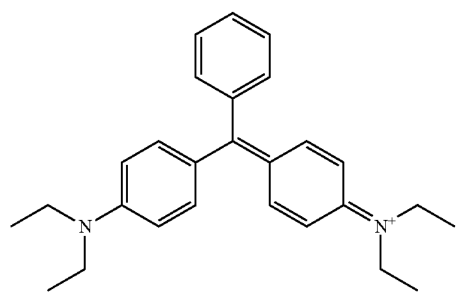 [SMILES: CCN(CC)c1ccc(C(=C2C=CC(=[N+](CC)CC)C=C2)c2ccccc2)cc1] |
| F13 | C. I. Basic Red 14 | 2.34<br>f¹ = 1.64 | 2.37 | yes | −36 | 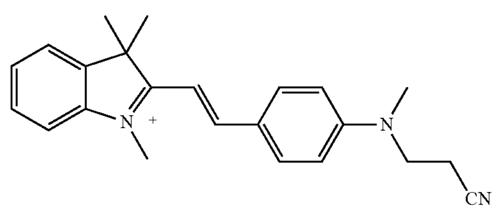 |
| F14 | C. I. Basic Orange 21 | 2.49<br>f¹ = 1.13 | 2.53 | yes | −36 | 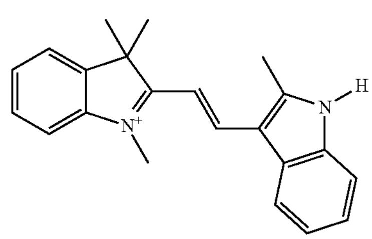 [SMILES: Cc1[nH]c2ccccc2c1/C=C/C1=[N+](C)c2ccccc2C1(C)C] |
| F15 | | 2.26<br>f¹ = 1.89 | 2.24 | yes | −34 | 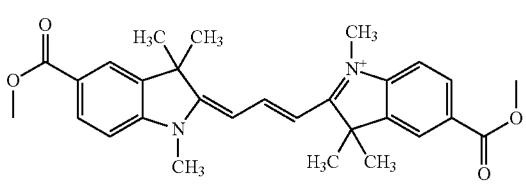 [SMILES: COC(=O)c1ccc2c(c1)C(C)(C)C(/C=C/C=C1/N(C)c3ccc(C(=O)OC)cc3C1(C)C)=[N+]2C] |

TABLE 2-continued

Theoretical and experimental absorption energies, theoretical absorption strengths (f¹) and coinitiation energies (see text) and experimental holographic activity of dyes in two-component initiator systems comprising CGI909.

| Dye example | Name | Absorption/eV Theory (E/f¹) | Exp. | Holographically active (yes/no) | E(CGI)/ (kJ/mol) | Structure |
|---|---|---|---|---|---|---|
| F16 | C. I. Basic Blue 3 | 1.94 f¹ = 1.30 | 1.89 | yes | −33 | 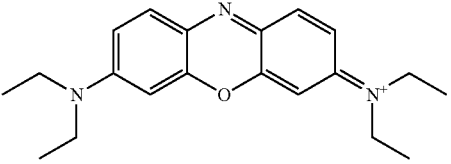 [SMILES: CCN(CC)c1ccc2nc3ccc(=[N+](CC)CC)cc-3oc2c1] |
| F17 | ethyl violet | 2.24 f¹ = 1.02 | 2.08 | yes | −30 | 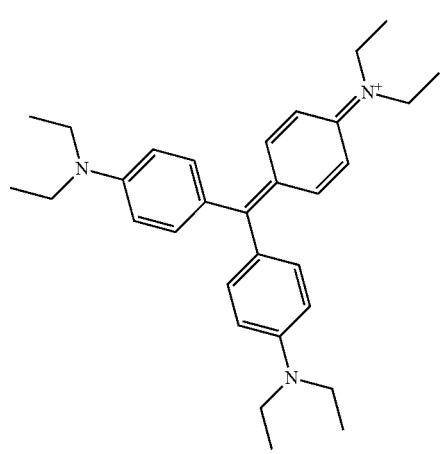 [SMILES: CCN(CC)c1ccc(C(=C2C=CC(=[N+](CC)CC)C=C2)c2ccc(N(CC)CC)cc2)cc1] |
| F18 | | 2.62 f¹ = 1.33 | 2.52 | yes | −26 | 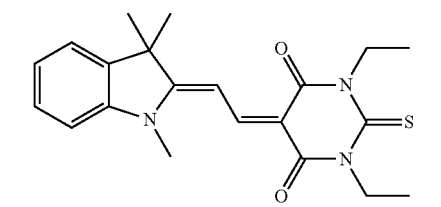 [SMILES: CCN1C(=O)C(=C/C=C2\N(C)c3ccccc3C2(C)C)C(=O)N(CC)C1=S] |
| F19 | EAB | 3.29 f¹ = 1.14 | 3.53 | yes | −23 | 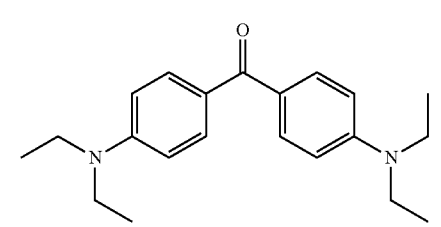 [SMILES: CCN(CC)c1ccc(C(=O)c2ccc(N(CC)CC)cc2)cc1] |
| F20 | C. I. Basic Violet 16 | 2.28 f¹ = 1.69 | 2.19 | yes | −18 | 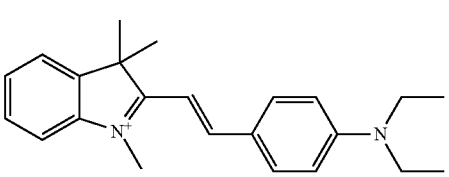 [SMILES: CCN(CC)c1ccc(/C=C/C2=[N+](C)c3ccccc3C2(C)C)cc1] |
| F21 | | 2.65 f¹ = 1.46 | 2.58 | yes | −14 | 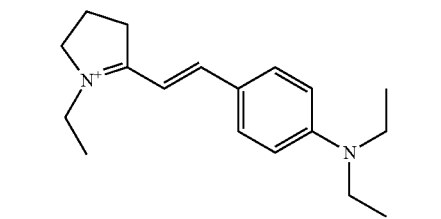 [SMILES: CCN(CC)c1ccc(/C=C/C2=[N+](CC)CCC2)cc1] |

TABLE 2-continued

Theoretical and experimental absorption energies, theoretical absorption strengths (f¹) and coinitiation energies (see text) and experimental holographic activity of dyes in two-component initiator systems comprising CGI909.

| Dye example | Name | Absorption/eV Theory (E/f¹) | Exp. | Holographically active (yes/no) | E(CGI)/ (kJ/mol) | Structure |
|---|---|---|---|---|---|---|
| F22 | | 2.39<br>f¹ = 1.62 | 2.52 | no | 3 | 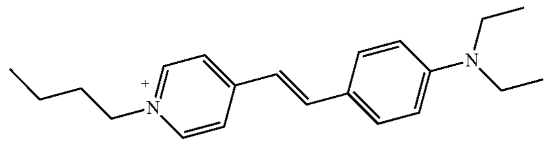 |
| F23 | C. I. Basic Yellow 28 | 2.57<br>f¹ = 1.10 | 2.76 | no | 5 | 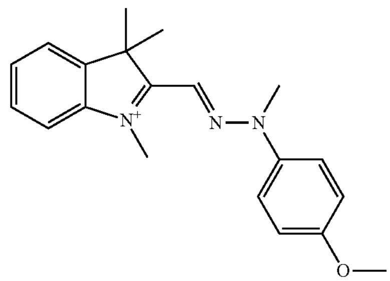 [SMILES: COc1ccc(N(C)/N=C/C2=[N+](C)c3ccccc3C2(C)C)cc1] |
| F24 | | 2.47<br>f¹ = 1.56 | 2.51 | no | 7 | 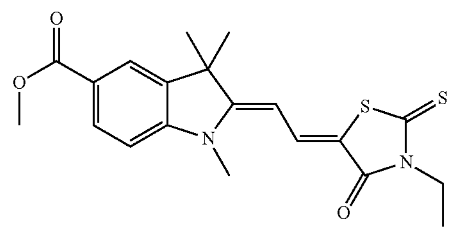 [SMILES: CCN1C(=O)/C(=C/C=C2\N(C)c3ccc(C(=O)OC)cc3C2(C)C)SC1=S] |
| F25 | pinacyanol | 2.05<br>f¹ = 2.03 | 2.05 | no | 7 | 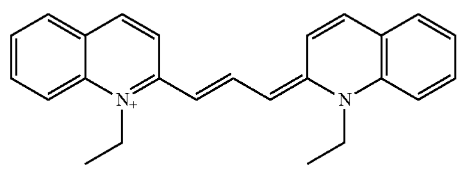 [SMILES: CCN1/C(=C/C=C/c2ccc3ccccc3[n+]2CC)C=Cc2ccccc21] |
| F26 | | 2.62<br>f¹ = 1.52 | 2.64 | no | 21 | 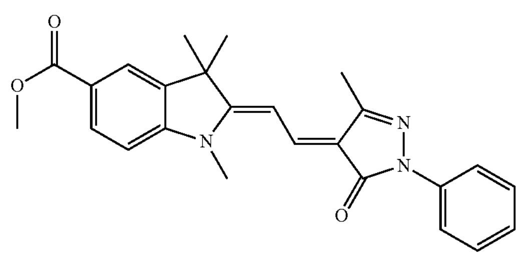 [SMILES: COC(=O)c1ccc2c(c1)C(C)(C)/C(=C/C=C1/C(=O)N(c3ccccc3)N=C1C)N2C] |
| F29 | | 2.04<br>f¹ = 2.05 | 1.95 | no | 1 | 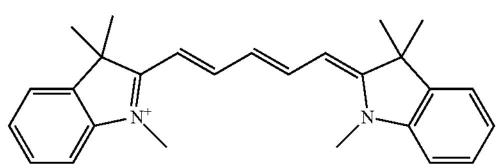 [SMILES: CN1\C(=C/C=C/C=C/C2=[N+](C)c3ccccc3C2(C)C)C(C)(C)c2ccccc21] |
| F30 | | 2.00<br>f¹ = 2.34 | 1.91 | yes | −17 | 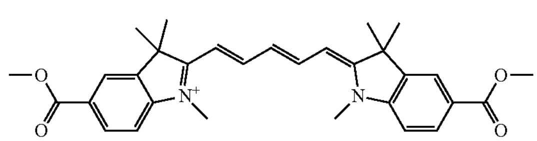 |

Dye example F5 was prepared similarly to EP 0 671 393.

Dye example F6 was prepared as described in Ronald Flaig's 1996 dissertation.

Dye example F9 is known from WO 9514689 and commercially available in 2012 from Spectra Group Limited, Inc, 27800 Lemoyne Road Suite J, Millbury, Ohio 43447, USA.

Dye example F11 was prepared similarly to U.S. Pat. No. 3,573,289.

Dye example F15 was prepared similarly to EP 58 863.

Dye examples F18, F24 and F26 were prepared similarly to Synthesis, 1999, 2103.

Dye example F21 was prepared similarly to DE 883 025.

Dye example F22 was prepared as described in J. Chem. Soc. 1938, 1454.

Dye example F29 was prepared as described in Proceedings of the Imperial Academy (Tokyo), 1932, vol. 8, p. 421 (Chem. Zentralbl., 1934, vol. 105, # II p. 2227).

Dye example F30 was prepared similarly to Example 29.

Example 2

The operating assumption is that, for a given task, the photopolymer formulation is to be exposed with laser light having a wavelength of 530 nm. The method of the present invention will now be used to verify the suitability of the three-component initiator system dye F1/Irgacure® 250/EDB for the application described.

The reaction mechanism of the dye F1/Irgacure® 250/EDB three-component initiator system consists of the following steps:

1. Light absorption by the dye. With transition from the electronic ground state ($S_0$) into the first excited singlet state ($S_1$).
2. Intersystem crossing into a triplet state of the dye and fast relaxation to the lowest triplet state ($T_1$).
3. Reaction of the dye molecule in the $T_1$ state with Irgacure® 250 to form methyl-1-iodo-4-isobutylbenzene IPh$^i$Bu and a toluyl free-radical.
4. Reaction of the toluyl free-radical Tol$_{rad}$ with ethyl 4-dimethylaminobenzoate (EDB) to form toluene and the corresponding EDB free-radical EDB$_{rad}$.

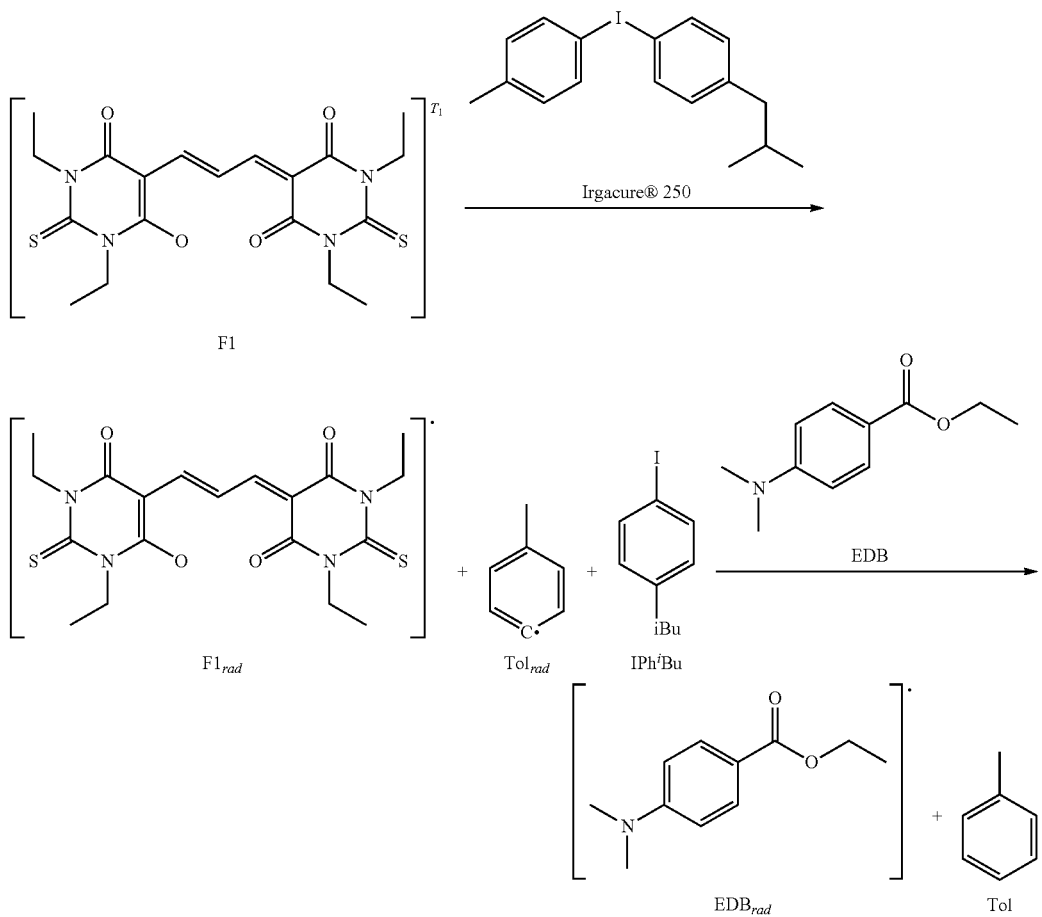

Reaction Mechanism of the Dye F1/Irgacure® 250/EDB Three-Component Initiator System The three-dimensional structures of dye F1, Irgacure® 250, EDB and also of the decomposition products of Irgacure® 250 and the free radical derived from EDB by H abstraction were subjected to a conformer analysis by means of the conformer module in the Materials Studio software package from Accelrys. The result of this analysis was that, in the present case, only the stablest conformer had to be considered in each case. Therefore, the stablest conformer according to the force field computation performed in the conformer analysis was used in each case as starting point for the quantum-chemical computations.

The particular stablest conformers thus found were then geometrically optimized quantum-chemically in the electronic ground state in accordance with step d) of the method according to the present invention. This was done using the TURBOMOLE Version 6.1 software package. The computations were done on a density-functional theoretical level using the density functional BP86 and the base set TZVP. The COnductor like Screening MOdel (COSMO) continuum solvent model was also used. The molecular geometries thus obtained were then subjected to single point computations at the BH-LYP/TZVP+COSMO level. The result of this computation, i.e. absolute electronic energies at the DFT(BH-LYP/TZVP+COSMO//BP86/TZVP+COSMO) level (see Table 3), is used as described hereinbelow to compute the reaction energies of the initiation reaction.

TABLE 3

Absolute electronic ground state energies of the compounds involved in the dye F1/Irgacure ® 250/EDB initiation reaction

| Compound | E(BH-LYP/TZVP + COSMO//BP86/TZVP + COSMO)/Hartree |
|---|---|
| Irgacure ® 250 | −670.781969 |
| dye F1$_{rad}$ | −2053.882516 |
| Tol$_{rad}$ | −270.795918 |
| IPh$^i$Bu | −400.140492 |
| EDB | −633.254506 |
| EDB$_{rad}$ | −632.603044 |
| Tol | −271.481294 |

The next step (step e)) involved computing the electronic excitation energy of F1 by means of time-dependent density functional theory and using the BH-LYP hybrid functional and the TZVP base set and also the COSMO model. The excitation energy turned out to be 2.98 eV and the oscillator strength (as per the long form of the dipole operator) as 1.63 units. The excitation energy is corrected for its systematic error of 0.56 eV, determined empirically on a large benchmark set of dyes, to 2.42 eV, which corresponds to a wavelength of 512 nm.

The last remaining energy to be computed is the absolute energy of the first triplet state of F1. This is likewise done on the DFT(BH-LYP/TZVP+COSMO//BP86/TZVP+COSMO) level and produced an energy of $E(^3F1)=-2054.000848$ Hartree.

The intersystem crossing of the dye from $S_0$ into the $T_1$ state is consistently negative. This means that, in the above-described reaction mechanism, only the reaction of dye F1 with Irgacure® 250 ($E_{coin,1}$), and also the subsequent reaction with EDB ($E_{coin,2}$) of the toluyl free-radical resulting from the Irgacure® 250 decomposition are relevant for the three-component initiator system. These are apparent from the computed absolute energies as follows:

$$E_{coin,1} = E(F1_{rad}) + E(Tol_{rad}) + E(IPh^iBu) - E(^3F1) - E(\text{Irgacure} ® \ 250)$$
$$= (-2053.882516 - 270.795918 - 400.140492 +$$
$$2054.000848 + 670.781969)\text{Hartree}$$
$$= -0.036109 \text{ Hartree}$$
$$\approx -95 \text{ kJ/mol}$$

$$E_{coin,2} = E(EDB_{rad}) + E(Tol) - E(Tol_{rad}) - E(EDB)$$
$$= (-632.603044 - 271.481294 + 270.795918 + 633.254506)\text{Hartree}$$
$$= -0.033913 \text{ Hartree}$$
$$\approx -89 \text{ kJ/mol}$$

Since both the reaction energies are negative, the computed absorption energy at 512 nm is within the tolerance interval of ±50 nm around the target value of 530 nm and the excitation at an oscillator strength of 1.63 units is above the threshold value of 0.2, the three-component initiator system dye F1/Irgacure® 250/EDB must be classified as suitable according to step h) of the method according to the present invention.

The photoinitiator system proved to be holographically active in agreement with the prediction and also the computed absorption wavelength of 512 nm shows good agreement with the experimental value of 531 nm.

Table 4 shows further examples computed in a similar manner. $E_{coin,2}$ was not reported therein since it is independent of the dye and therefore corresponds to Example 2 for all three-component photoinitiator systems. The preparation and testing of Example Medium 2 were repeated on media comprising the particular dyes indicated in Table 4, which likewise shows the results obtained with the method of the present invention.

TABLE 4

Theoretical and experimental absorption energies and coinitiation energies (see text) and experimental holographic activity of dyes in three-component initiator systems comprising Irgacure ® 250 and EDB.

| Dye example | Name | Absorption/eV Theory | Exp. | Holographically active (yes/no) | $E_{Coin,1}$/ (kJ/mol) | Structure |
|---|---|---|---|---|---|---|
| F1 | | 2.42 $f^1 = 1.63$ | 2.33 | yes | −95 | 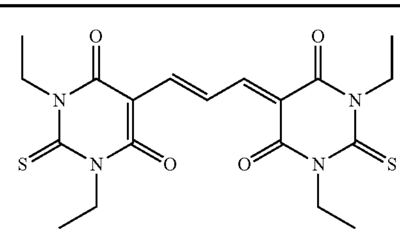 |

TABLE 4-continued

Theoretical and experimental absorption energies and coinitiation energies (see text) and experimental holographic activity of dyes in three-component initiator systems comprising Irgacure ® 250 and EDB.

| Dye example | Name | Absorption/eV Theory | Exp. | Holographically active (yes/no) | $E_{Coin,1}/$ (kJ/mol) | Structure |
|---|---|---|---|---|---|---|
| F2 | Ketocoumarin | 2.64 $f^1 = 1.90$ | 2.70 | yes | −131 | 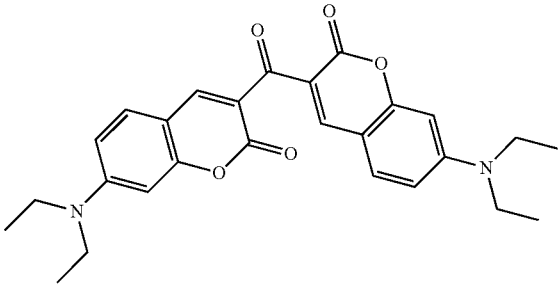 [SMILES: CCN(CC)c1ccc2cc(C(=O)c3cc4ccc(N(CC)CC)cc4oc3=O)c(=O)oc2c1] |
| F3 | Carbol Fuchsin | 2.41 $f^1 = 0.79$ | 2.24 | no | 0 | 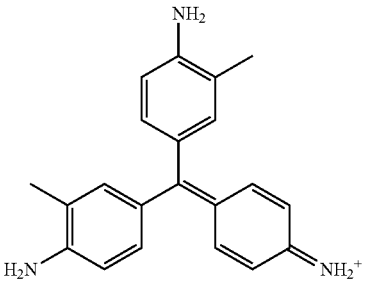 [SMILES: Cc1cc(C(=C2C=CC(=[NH2+])C=C2)c2ccc(N)c(C)c2)ccc1N] |
| F9 | | 2.64 $f^1 = 1.00$ | 2.64 | yes | −31 | 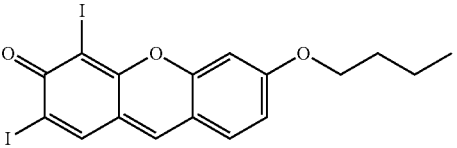 [SMILES: CCCCOc1ccc2cc3cc(I)c(=O)c(I)c-3oc2c1] |
| F10 | Safranine O | 2.37 $f^1 = 0.97$ | 2.32 | yes | −33 | 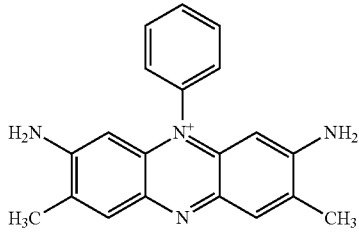 [SMILES: Cc1cc2nc3cc(C)c(N)cc3[n+](-c3ccccc3)c2cc1N] |
| F18 | | 2.62 $f^1 = 1.33$ | 2.52 | yes | −84 | 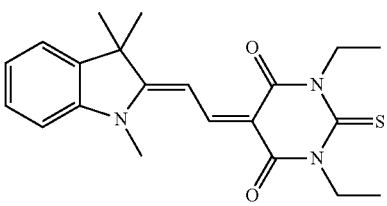 [SMILES: CCN1C(=O)C(=C/C=C2\N(C)c3ccccc3C2(C)C)C(=O)N(CC)C1=S] |
| F19 | EAB | 3.29 $f^1 = 1.14$ | 3.53 | yes | −187 | 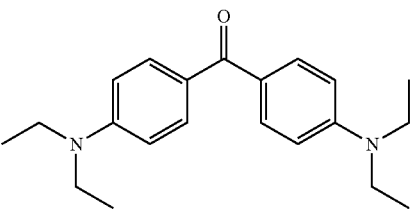 [SMILES: CCN(CC)c1ccc(C(=O)c2ccc(N(CC)CC)cc2)cc1] |

TABLE 4-continued

Theoretical and experimental absorption energies and coinitiation energies (see text) and experimental holographic activity of dyes in three-component initiator systems comprising Irgacure ® 250 and EDB.

| Dye example | Name | Absorption/eV Theory | Exp. | Holographically active (yes/no) | $E_{Coin,1}$/ (kJ/mol) | Structure |
|---|---|---|---|---|---|---|
| F27 | | 2.33 $f^1 = 1.80$ | 2.22 | yes | −99 | 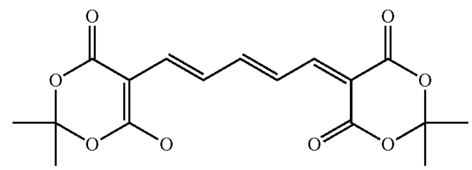 |
| F28 | | 2.11 $f^1 = 0.63$ | 1.95 | no | 182 | 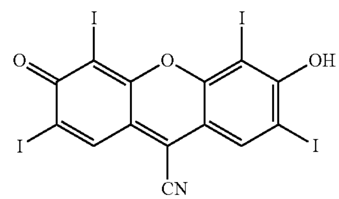 [SMILES: N#Cc1c2cc(I)c(=O)c(I)c-2oc2c(I)c(O)c(I)cc12] |

Dye example F27 was prepared similarly to EP 1 253 148.
Dye example F28 is known from WO 9514689 and commercially available in 2012 from Spectra Group Limited, Inc, 27800 Lemoyne Road Suite J, Millbury, Ohio 43447, USA.

Quality of Prediction for Excitation Energies of Contemplated Examples:

The errors in the prediction of $\lambda_{max}$ for Examples 1 and 2 described at length above are small at 0.02 eV (Example 1) and 0.09 eV (Example 2). FIG. 3 shows that this is also true of the other example dyes.

The excitation energy of EAB is an underestimate at 0.24 eV, which constitutes the maximum error within the set of examples investigated here, and the mean square deviation is 0.1 eV. These very small values are an indication the procedure is sufficiently accurate for use in the method of the present invention.

The invention claimed is:

1. A method of selecting photoinitiator systems for photopolymer formulations, said method comprising
   a) selecting a photoinitiator system comprising at least one sensitizer and at least one coinitiator,
   b) establishing the photoinitiator system's reaction mechanism to include the transition of the sensitizer or sensitizers into an electronically excited state or, respectively, electronically excited states by absorption of electromagnetic radiation and the reaction which is referred to as the initiation reaction in subsequent steps whereby the sensitizer in the electronically excited state or the sensitizers in electronically excited states react(s) with the coinitiator(s) to form at least one free radical and further products, these products being dependent on the particular photoinitiator system,
   c) generating the three-dimensional molecular geometries of the sensitizer(s), of the coinitiator(s) and also of all initiation reaction intermediate and end products defined by the reaction mechanism and then subjecting these to a conformer analysis on the basis of a force field method,
   d) optimizing the molecular geometries of the structures from step c) having the lowest relative force field energy in each case quantum-chemically in the electronic ground state and determining the absolute electronic energies of the optimized structures,
   e) computing the excitation energies and oscillator strengths of the electronic absorption spectrum of the sensitizer(s) using the quantum-chemical time-dependent density-functional theory method and correcting the excitation energies for their systematic error,
   f) optimizing the molecular geometries of all sensitizers in the excited electronic states relevant with regard to the coinitiation reaction, on a density-functional theoretical level and determining the absolute electronic energies,
   g) computing the reaction energies of all component reactions of the mechanism established in step b), and
   h) classifying the photoinitiator system as suitable when the excitation frequency determined in step e) is in a ±50 nm interval around the exposure light wavelength and has an oscillator strength greater than 0.2 and when at the same time all reactive energies computed under g) are negative.

2. A method according to claim 1, characterized in that the quantum-chemical geometric optimizations in steps d) and f) are effected using the DFT(BP86/TZVP) method and then DFT(BH-LYP/TZVP) single point computations are carried out.

3. A method according to claim 1, characterized in that the quantum-chemical computations are carried out using the COnductor like Screening MOdels (COSMO).

4. A method according to claim 1, characterized in that step e) utilizes the time-dependent DFT(BH-LYP/TZVP) procedure to compute the absorption spectra.

5. A method according to claim 4, characterized in that the time-dependent DFT computations are carried out using the COnductor like Screening MOdels (COSMO).

6. A method according to claim 5, characterized in that the systematic error in step e) is assumed to be +0.56 electronvolt.

7. A method according to claim 4, characterized in that the systematic error in step e) is assumed to be +0.7 electronvolt.

8. A method according to claim 1, characterized in that steps d) and f) consider all molecular geometries in a force field energy window of 0-8 kJ/mol instead of just the molecular geometry having the lowest force field energy and Boltzmann-weighted mean excitation energies, absorption strengths and overall energies are used not only to compute the absorption spectrum of the sensitizer in step e) but also to determine the reaction energies in step g), the Boltzmann weights being computed on a density-functional theoretical level, more preferably on the basis of DFT(BP86/TZVP) geometric optimizations with subsequent DFT(BH-LYP/TZVP) single point computations each using COSMO.

* * * * *